United States Patent
Chan et al.

(10) Patent No.: US 10,643,319 B2
(45) Date of Patent: May 5, 2020

(54) APPARATUS AND METHOD FOR CONTEXT-ORIENTED BLENDING OF RECONSTRUCTED IMAGES

(71) Applicant: Canon Medical Systems Corporation, Otawara-shi (JP)

(72) Inventors: Chung Chan, Stamford, CT (US); Zhou Yu, Wilmette, IL (US); Jian Zhou, Buffalo Grove, IL (US)

(73) Assignee: Canon Medical Systems Corporation, Otawara-shi (JP)

( * ) Notice: Subject to any disclaimer, the term of this patent is extended or adjusted under 35 U.S.C. 154(b) by 284 days.

(21) Appl. No.: 15/884,089

(22) Filed: Jan. 30, 2018

(65) Prior Publication Data
US 2019/0236763 A1 Aug. 1, 2019

(51) Int. Cl.
*G06T 5/50* (2006.01)
*G06T 5/00* (2006.01)
(Continued)

(52) U.S. Cl.
CPC ............ *G06T 5/50* (2013.01); *A61B 6/032* (2013.01); *A61B 6/463* (2013.01); *A61B 6/5235* (2013.01);
(Continued)

(58) Field of Classification Search
USPC .................................................. 382/131, 275
See application file for complete search history.

(56) References Cited

U.S. PATENT DOCUMENTS 7,809,178 B2 * 10/2010 Spies ....................... G06T 5/50
382/128
7,991,243 B2 * 8/2011 Bal ....................... G06T 11/008
378/21
(Continued)

FOREIGN PATENT DOCUMENTS

CN 103959329 B 10/2017

OTHER PUBLICATIONS

Flicek et al., "Reducing the Radiation Dose for CT Colography Using Adaptive Statistical Interative Reconstruction: A Pilot Study," AJR: 195, Jul. 2010.
(Continued)

*Primary Examiner* — Ishrat I Sherali
(74) *Attorney, Agent, or Firm* — Oblon, McClelland, Maier & Neustadt, L.L.P.

(57) ABSTRACT

A method and apparatus is provided generate a display image that optimize a tradeoff between resolution and noise by using blending weights/ratio based on the content/context of the image. The blending weights control the relative weights when combining multiple computed tomography (CT) images having different degrees of smoothing/denoising to generate a display image having the optimal tradeoff lying within the continuum between/among the CT images. The blending weights are automated based on information indicating the content/context of the display image (e.g., the segmented tissue type, average attenuation, and the display setting such as window width and window level). Thus, indicia indicating content/context of the image determine the weighting coefficients, which are used in a weighted sum, e.g., to combine the plurality of images with different noise/smoothing parameters into a single blended image, which is displayed.

20 Claims, 11 Drawing Sheets

(51) Int. Cl.
*G06T 11/00* (2006.01)
*A61B 6/03* (2006.01)
*A61B 6/00* (2006.01)

(52) U.S. Cl.
CPC ............ *A61B 6/5258* (2013.01); *G06T 5/002* (2013.01); *G06T 11/006* (2013.01); *G06T 11/008* (2013.01); *G06T 2207/10081* (2013.01); *G06T 2207/20216* (2013.01); *G06T 2207/30016* (2013.01); *G06T 2207/30061* (2013.01); *G06T 2210/41* (2013.01); *G06T 2211/424* (2013.01)

(56) References Cited

U.S. PATENT DOCUMENTS

| | | | | |
|---|---|---|---|---|
| 8,280,135 | B2* | 10/2012 | McCollough | A61B 6/032 378/4 |
| 8,605,970 | B2* | 12/2013 | Bar-Aviv | G06T 5/50 378/4 |
| 10,282,872 | B2* | 5/2019 | Dennerlein | G06T 5/002 |
| 2008/0152203 | A1* | 6/2008 | Bal | G06T 11/008 382/131 |
| 2008/0285881 | A1* | 11/2008 | Gal | G06T 5/20 382/261 |
| 2012/0059252 | A1* | 3/2012 | Li | A61B 6/032 600/425 |
| 2017/0109904 | A1* | 4/2017 | Huang | G06T 11/008 |
| 2019/0365341 | A1* | 12/2019 | Chan | A61B 6/032 |

OTHER PUBLICATIONS

Thibault et al., "A three-dimensional statistical approach to improved image quality for multislice helial CT," Medical Physics, vol. 34, No. 11, Nov. 2007.

Chang et al., "Metal Artifact Reduction Algorithm for Single Energy and Dual Energy CT Scans," IEEE Nuclear Science Symposium and Medical Imaging Conference Record, 2012.

Heimann et al., "Comparison and Evaluation of Methods for Liver Segmentation From CT Datasets," IEEE Transactions on Medical Imaging, vol. 28, No. 8, Aug. 2009.

Joseph Shtok, et al.; "Direct Adaptive Algorithms for CT Reconstruction" Computer Science Department, Technion-Israel Institute of Technology, Haifa 32000, Israel, 4 pages.

* cited by examiner

-2048                                                    1449

-2048                                          1449

-2048                                                                    1449

APPARATUS AND METHOD FOR CONTEXT-ORIENTED BLENDING OF RECONSTRUCTED IMAGES

FIELD

This disclosure relates to generating a blended image by blending reconstructed images of varying levels of soothing/denoising based on context information, and, more particularly, to using the context information to select the relative contributions of the reconstructed images to the blended image.

BACKGROUND

Computed tomography (CT) systems and methods are widely used, particularly for medical imaging and diagnosis. A CT scan can be performed by positioning a patient on a CT scanner in a space between an X-ray source and X-ray detector, and then taking X-ray projection images through the patient at different angles as the X-ray source and detector are rotated through a scan. The resulting projection data is referred to as a CT sinogram, which represents attenuation through the body as a function of position along one or more axis and as a function of projection angle along another axis. Performing an inverse Radon transform—or any other image reconstruction method—reconstructs an image from the projection data represented in the sinogram.

Various methods can be used to reconstruct CT images from projection data, including filtered back-projection (FBP) and statistical iterative reconstruction (IR) algorithms. Compared to more conventional FBP reconstruction methods, IR methods can provide improved image quality at reduced radiation doses. Various iterative reconstruction (IR) methods exist, such as the algebraic reconstruction technique. For example, one common IR method performs unconstrained (or constrained) optimization to find the argument p that minimizes the expression $$\arg\min_{p}\{\|Ap-\ell\|_W^2 + \beta U(p)\},$$

wherein $\ell$ is the projection data representing the logarithm of the X-ray intensity of projection images taken at a series of projection angles and p is a reconstructed image of the X-ray attenuation for voxels/volume pixels (or two-dimensional pixels in a two-dimensional reconstructed image) in an image space. For the system matrix A, each matrix value $a_{ij}$ (i being a row index and j being a column index) represents an overlap between the volume corresponding to voxel $p_j$ and the X-ray trajectories corresponding to projection value $\ell_i$. The data-fidelity term $\|Ap-\ell\|_W^2$ is minimized when the forward projection A of the reconstructed image p provides a good approximation to all measured projection images $\ell$. Thus, the data fidelity term is directed to solving the system matrix equation $Ap=\ell$, which expresses the Radon transform (i.e., projections) of various rays from a source through an object OBJ in the space represented by p to X-ray detectors generating the values of $\ell$ (e.g., X-ray projections through the three-dimensional object OBJ onto a two-dimensional projection image $\ell$).

The notation $\|g\|_W^2$ signifies a weighted inner product of the form, $g^T W g$, wherein W is the weight matrix (e.g., expressing a reliability of trustworthiness of the projection data based on a pixel-by-pixel signal-to-noise ratio). In other implementations, the weight matrix W can be replaced by an identity matrix. When the weight matrix W is used in the data fidelity term, the above IR method is referred to as a penalized weighted least squares (PLWS) approach.

The function U(p) is a regularization term, and this term is directed at imposing one or more constraints (e.g., a total variation (TV) minimization constraint) which often have the effect of smoothing or denoising the reconstructed image. The value β is a regularization parameter is a value that weights the relative contributions of the data fidelity term and the regularization term.

Consequently, the choice of the value for the regularization term β typically affects a tradeoff between noise and resolution. In general, increasing the regularization term β reduces the noise, but at the cost of also reducing resolution. The best value for the regularization term β can depend on multiple factors, the primary of which is the application for which the reconstructed image is to be reconstructed. Because IR algorithms can be slow and require significant computational resources, a cut-and-try approach is inefficient (e.g., different values of the regularization term β are used for the IR method until an optimal solution is obtained). Moreover, a single CT scan can be used for more than one clinical application, and, therefore, an ability to adjust the reconstructed image with regards the tradeoff between noise and resolution without repeating the computationally intensive IR algorithm is desirable. Thus, improved methods are desired for rapidly generating and modifying a reconstructed image to optimize a tradeoff between noise and resolution.

BRIEF DESCRIPTION OF THE DRAWINGS

A more complete understanding of this disclosure is provided by reference to the following detailed description when considered in connection with the accompanying drawings, wherein.

DETAILED DESCRIPTION

The methods provided herein address the above-discussed challenges with regards to optimizing a tradeoff between resolution and noise based on the particular content/context of a displayed image. These methods addressed the aforementioned challenges by, e.g., using content/context of an image to control the generation of a blended image that is a weighted combination of a two or more reconstructed images having different degrees of smoothing/denoising (also referred to as amounts or levels of smoothing/denoising) and the corresponding tradeoff in resolution. In certain implementations, the indicator of the image content/context can be a display setting (e.g., a slice thickness, window width, and/or window level selected by a user or by default), or the indicator of the image content can be a regional/segmented histogram of the Hounsfield Units (HU) or derivative thereof.

Figure 1A:
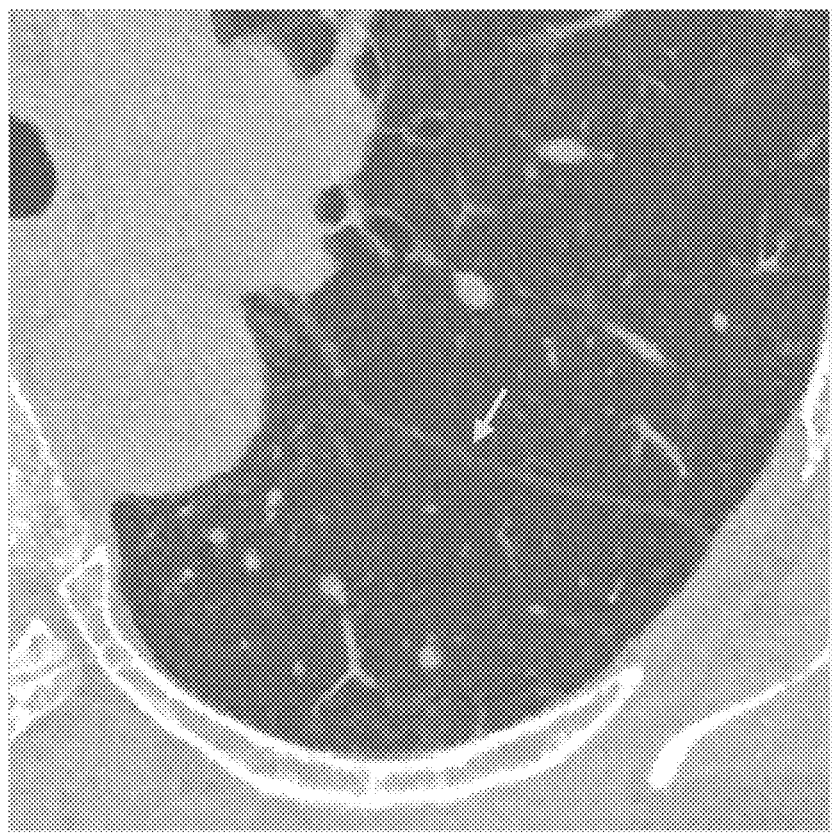
FIG. 1A shows an example of a lung region in slice of a reconstructed computed tomography (CT) image that was generated using a small smoothing/denoising parameter and that is displayed using lung settings (i.e., the window level is WL=−400 Hounsfield Units (HU) and the window width is WW=1500 HU), according to one implementation.
Figure 1B:
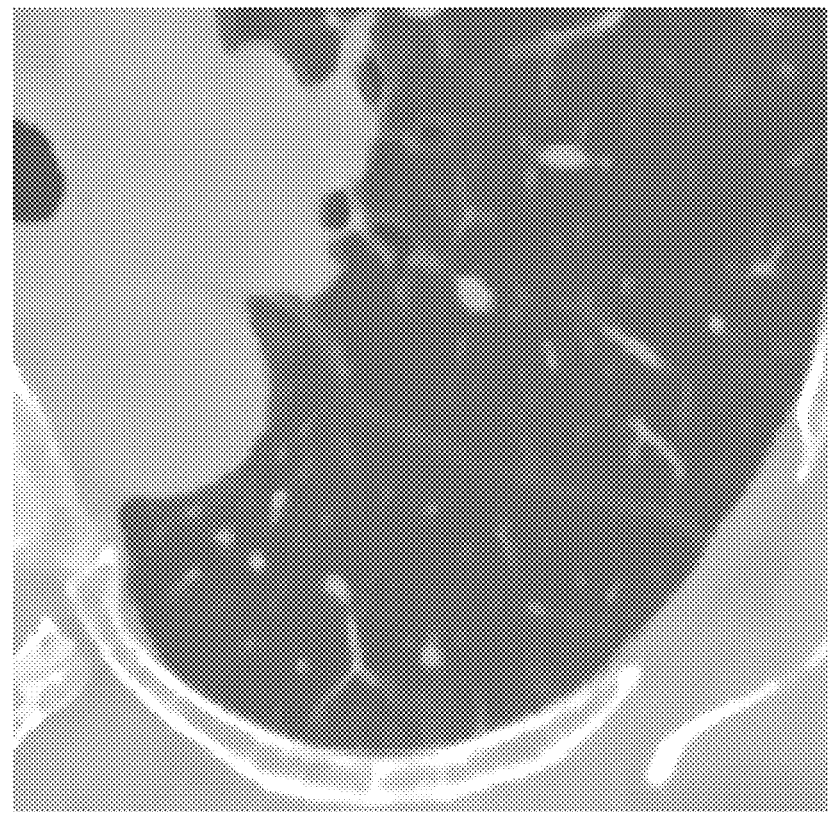
FIG. 1B shows an example of the same lung region using the same display settings as in FIG. 1A, except the CT image was generated using a large smoothing/denoising parameter rather than the small smoothing/denoising parameter used in FIG. 1A, according to one implementation.
Figure 2A:
FIG. 2A shows an example of a soft-tissue region in slice of the CT image that was generated using the small smoothing/denoising parameter and the image is displayed using soft-tissue settings (i.e., WL=40 HU and WW=400 HU), according to one implementation.
Figure 2B:
FIG. 2B shows an example of the same soft-tissue region and soft-tissue display settings as in FIG. 2A, except the CT image was generated using the large smoothing/denoising parameter, according to one implementation.
Figure 9:
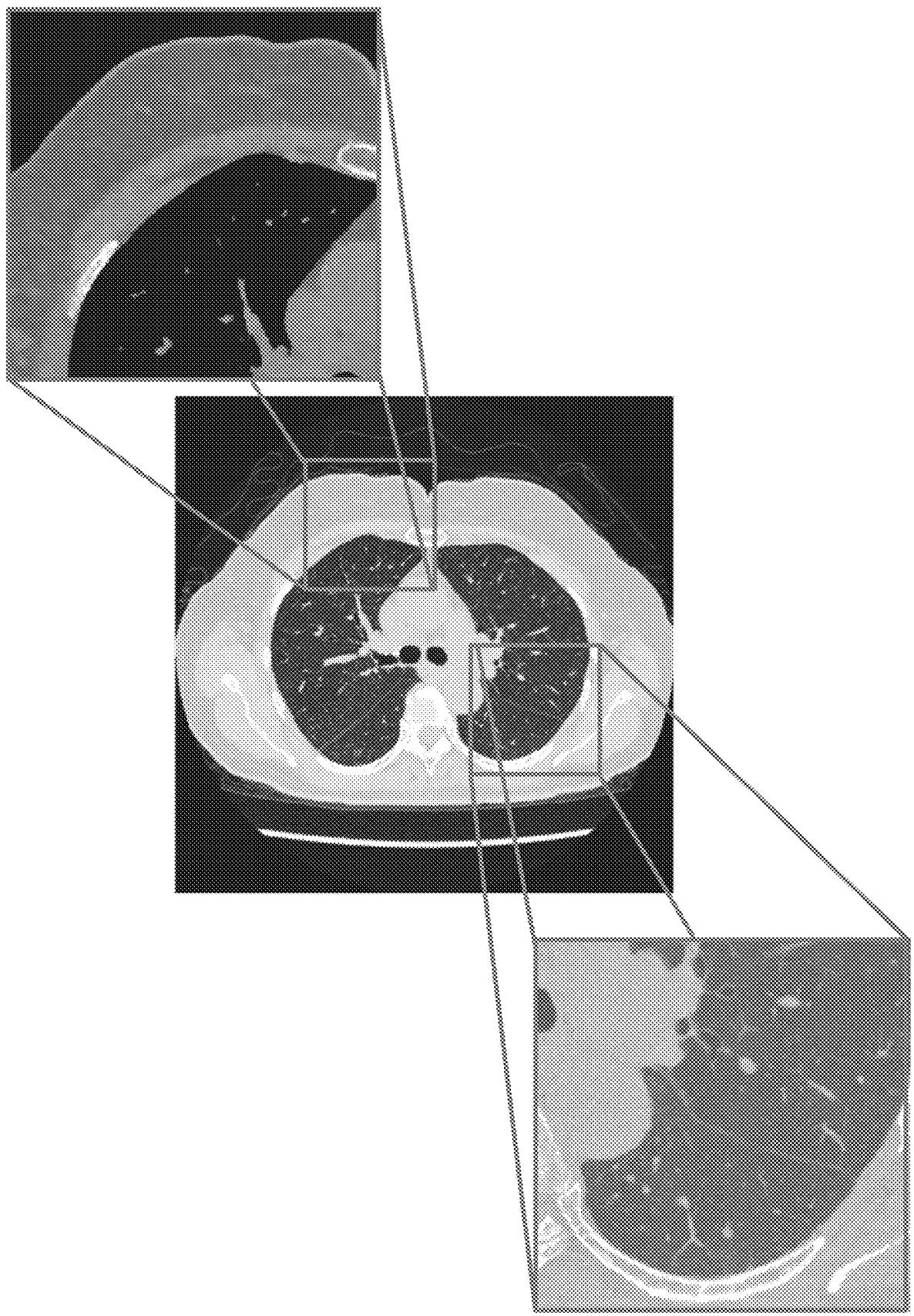
FIG. 9 shows a full 2D slice of the blended image (center) generated using the 2D map of the weighting value α from FIG. 8; superimposed on the full slice images are two zoomed-in images with a image of the soft-tissue region (upper left) and a zoomed-in image of the lung region (lower right) displayed respectively using the soft-tissue and lung window settings, according to one implementation.

Referring now to the drawings, wherein like reference numerals designate identical or corresponding parts throughout the several views, FIGS. 1A and 1B show two images of the same lung region but with different degrees of denoising (which herein is interchangeably referred to as smoothing). FIG. 9, which is discussed below, shows that this lung region is a part of a larger slice taken from a reconstructed image of a chest. Similarly, FIGS. 2A and 2B show two images of the same soft-tissue region with different degrees of denoising. FIGS. 1A and 2A represent a first degree of denoising, and FIGS. 1B and 2B represent a second degree of denoising with more denoising/smoothing than the first degree of denoising shown in FIGS. 1A and 2A.

In a comparison between FIGS. 2A and 2B, FIG. 2B is generally regarded as being better for clinical applications because the additional resolution in FIG. 2A does not convey significantly more information, but the additional noise in FIG. 2A creates texture and structure that is distracting and could potentially lead to a poor diagnosis or during an interventional procedure a poor outcome. Accordingly, a greater degree of denoising and smoothing can be beneficial for soft-tissue images.

In contrast, a lesser degree of denoising and smoothing can be beneficial for lung images. In a comparison between FIGS. 1A and 1B, FIG. 1A is generally regarded as being better for clinical applications because the additional resolution in FIG. 1A is significant to being able to distinguish the features of the lungs (e.g., the feature pointed to by the arrow in FIG. 1A), and, compared to the larger widow width in the lung settings and the commensurately higher contrast signals in the lung regions, the additional noise is not as significant as in the small-tissue region. Consequently, the additional noise due to less smoothing obscure relatively little in the lung region and that drawbacks of additional noise are outweighed by the benefits of the improved resolution as exhibited in FIG. 1A.

Thus, the degree of denoising can depend on the content/context of an image, or more particularly, the content of a region of interest within the reconstructed image. That is different regions within the same image can benefit from different degrees of denoising. Further, the benefit of the denoising can depend on the thickness of the slice of the image. For example, a thicker slice averages together more layers of voxels from the reconstructed image, and, under an assumption of statistical independent noise between voxels of the reconstructed images, the signal-to-noise ratio (SNR) can be expected to grow as the square root of the number voxels being averaged. Thus, when the image displayed is a thicker slice, less denoising/smoothing is required in order to achieve the same degree of noise suppression and SNR. Accordingly, in certain implementations, the methods herein use the thickness of the slice in addition to other indicia of the content/context when determining the relative weights between high- and low-denoising images that are combined to generate a blended image.

A blended image can be a weighted combination of images with different degrees of denoising. For example, through a weighted sum of two images (one having a low degree of denoising and the other having a high degree of denoising) a blended image can be generated to have any degree of denoising between these two originally images. This continuum for tuning the tradeoff between noise and resolution is achieved, e.g., by adjusting their relative weights in the sum. In certain implementations, these relative weights can vary as a function of position to represent spatial variations in the content of the reconstructed image (e.g., by segmenting the reconstructed image into lung regions and soft-tissue regions).

The original images having different degrees of denoising can be obtained by various means. For example, as discussed above, different values for the regularization parameter β can be used during an IR method. But this is not the only way to generate images with different degrees of denoising/smoothing, and additional methods of denoising can be applied during image reconstruction as well as before and after image reconstruction and/or any combination thereof using any of the methods described below or the IR method described above.

Various methods can be used to minimize noise in images that are reconstructed from computed tomography (CT) projection data. For example, post-processing (i.e., post-reconstruction) denoising methods can be applied to the data after the reconstructed image has been generated. Additionally, when an image is reconstructed using an IR method, which minimizes a cost function having both a data fidelity term and a regularization, the amount of noise in the reconstructed image and the statistical properties of the noise can depend on the type of regularizer and the magnitude of the regularization parameter $\beta$. As the regularization parameter $\beta$ becomes larger, the regularization term is emphasized more relative to the data fidelity tem, reducing the noise in the reconstructed image. However, this increased emphasis on the regularization term can also decrease the resolution and contrast, which is especially noticeable for fine and low-contrast features, such as those common in the lungs, as discussed above.

In general, the parameter $\beta$ is used herein as an identifier to represent a general smoothing and/or denoising parameter to characterize the degree of smoothing/denoising of a given reconstructed image, whether or not the degree of smoothing/denoising arises from the value of regularization parameter, a pre-processing (pre-reconstruction) method, a post-processing (post-reconstruction) method, or combination thereof. Context will make clear those instances when the parameter $\beta$ specifically refers to the regularization parameter, as opposed to referring more generally to an identifier of the type or degree of denoising/smoothing.

At various points below the generation of blended images is illustrated using a non-limiting example of a stack having only two images. Further, the blended image $p^{(Blended)}$ is a weighted sum of a small-smoothing-parameter image $p^{(\beta S)}$ and a large-smoothing-parameter image $p^{(\beta L)}$, and the small- and large-smoothing-parameter images are identical in all aspects including being reconstructed using the same IR method, except for using different values for the regularization parameter $\beta$ in the cost function of the IR method.

More generally, the stack of images can include more than two images. Further, the stack of images can be variously combined (e.g., as a weighted algebraic or geometric average) to create the blended image, accordingly to desired characteristics. In its simplest form, this combining of the stack of images can be performed as a weighted sum in which the weights add up to a constant value (e.g., the weights are normalized to sum to the value one).

Additionally, it is contemplated that the stack of images corresponding to greater and lesser denoising/smoothing amounts can be generated using various post- and or pre-reconstruction denoising methods, reconstruction methods that integrate denoising (e.g., through the selection of regularizer), or a combination of denoising integrated with the reconstruction method together with post- and/or pre-reconstruction denoising methods. Each of the denoising methods described below can be applied, e.g., to the sinogram/projection data prior to reconstruction or to a reconstructed image after reconstruction, and some of the denoising methods described below can also be applied to a reconstructed image between iterations of an IR method. As described below, the various denoising methods can include linear smoothing filters, anisotropic diffusion, non-local means, and nonlinear filters.

Linear smoothing filters remove noise by convolving the original image with a mask that represents a low-pass filter or smoothing operation. For example, the Gaussian mask comprises elements determined by a Gaussian function. This convolution brings the value of each pixel into closer agreement with the values of its neighbors. In general, a smoothing filter sets each pixel to the average value, or a weighted average, of itself and its nearby neighbors: the Gaussian filter is just one possible set of weights. Disadvantageously, smoothing filters tend to blur an image because pixel intensity values that are significantly higher or lower than the surrounding neighborhood are smeared or averaged across their neighboring area. Sharp boundaries become fuzzy. Generally, local linear filter methods assume that local neighbourhood are homogeneous, and local linear filter methods, therefore, tend to impose homogeneity on the image obscuring non-homogeneous features, such as lesions or organ boundaries.

Anisotropic diffusion removes noise while preserving sharp edges by evolving an image under a smoothing partial differential equation similar to the heat equation. If the diffusion coefficient were spatially constant, this smoothing would be equivalent to linear Gaussian filtering, but when the diffusion coefficient is anisotropic according to the presence of edges, the noise can be removed without blurring the edges of the image.

A median filter is an example of a nonlinear filter and, if properly designed, a nonlinear filter can also preserve edges and avoid blurring. A median filter operates, for example, by evaluating each pixel in the image, sorting the neighboring pixels according to intensity, and replacing the original value of the pixel with the median value from the ordered list of intensities. The median filter is one example of a rank-conditioned rank-selection (RCRS) filter. For example, median filters and other RCRS filters can be applied to remove salt and pepper noise from an image without introducing significant blurring artifacts.

In addition a filter using a total-variation (TV) minimization regularization term can be used where it is assumed that the areas being imaged are uniform over discrete areas with relatively sharp boundaries between the areas. A TV filter is another example of a nonlinear filter.

In non-local means filtering, rather than performing a weighted average of pixels according to their spatial proximity, pixels are determined to be a weighted average according to the similarity between patches within the images. Thus, noise is removed based on non-local averaging of all the pixels in an image—not just the neighboring pixels. In particular, the amount of weighting for a pixel is based on the degree of similarity between a small patch centered near that pixel and another small patch centered on the pixel being denoised.

In addition to the denoising methods discussed above, various degrees of denoising/smoothing can be achieved through a choice of regularizer and IR method. Additionally, regularization can be expressed as a constraint. For example, enforcing positivity for the attenuation coefficients can provide a level of regularization based on the practical assumption that there are no regions in the object OBJ that cause an increase (i.e., gain) in the intensity of the X-ray radiation.

Other regularization terms can similarly rely on a priori knowledge of characteristics or constraints imposed on the reconstructed image. For example, minimizing a TV regularizer in conjunction with projection on convex sets (POCS) can be used to achieve desirable image characteristics in many clinical imaging applications. The TV regularizer can be incorporated into the cost function, e.g., $$\arg\min_{p} \{\|Ap - \ell\|_W^2 + \beta\|p\|_{TV}\},$$

wherein $\|p\|_{TV} = \|\nabla p\|_1$ is the $\ell_1$-norm of the gradient-magnitude image, which is the isotropic TV semi-norm. The spatial-vector image $\nabla p$ represents a discrete approximation to the image gradient. Alternatively, some regularizer can be imposed as constraints. For example, a combination of TV and POCS regularization are imposed as constraints when the optimization problem is framed as $$p^* = \arg\min_{p} \|Ap - \ell\|_W^2 \text{ s.t. } \|p\|_{TV} \leq \beta \text{ and } p_j \geq 0.$$

So far the data fidelity term in the cost function has been for post-log projection data. Alternatively, a pre-log data fidelity term can be used, e.g., when the X-ray flux onto the detectors is low. In the discussion below the symbol $y \propto \exp(\ell)$ is used to represent the pre-log projection data. After preprocessing the X-ray detector counts to account for calibrations and data corrections (e.g., beam-hardening, detector nonlinearities, k escape, pileup, etc.), CT data can, in practice, be modeled by independent random variables following a Poisson distribution with additive Gaussian distribution to account for electronic noise in the measurement. The statistical model of the random variable $Y_i$ measured by the detector element i can be described as $$Y_i \sim \text{Poisson}(\bar{y}_i(p)) + \text{Gaussian}(0, \sigma_o^2)$$

wherein $\sigma_o^2$ denotes the standard deviation of electronic noise. The value $\bar{y}_i(p)$ is the expected pre-log projection data related to the attenuation image p by means of a nonlinear transformation, which is given by $$\bar{y}_i(p) = b_i \exp(-[Ap]_i) + r_i$$

wherein $b_i$ is a calibration factor of the detector element i determined, e.g., during a calibration scan, and $r_i$ is the mean of background measurement scattered photons). In pre-log methods, the attenuation image p can be reconstructed, e.g., from the measurement y using a complex likelihood function or from the shifted data $$\hat{Y}_i = [Y_i + \sigma_o^2]_+ \sim \text{Poisson}(\bar{y}_i(p) + \sigma_o^2),$$

using the tractable shifted-Poisson model, wherein $[\cdot]_+$ is a threshold function that sets negative values to zero. Alternatively, the shifted-Poisson model can be matched with that of the Poisson-Gaussian model, or the statistical model can be a Poisson model, a compound Poisson model, or any other statistical distribution or combination of statistical distribution representing the noise in the system. For the shifted-Poisson model, the image estimate is obtained by maximizing the log likelihood function of the shifted-Poisson model, which is given by $$p^* = \arg\max_{p \geq 0} \sum_i [\hat{y}_i \log(\bar{y}_i(p) + \sigma_o^2) - (\bar{y}_i(p) + \sigma_o^2)] - \beta U(p),$$

wherein U(p) is a regularizer that represents an image roughness penalty. For example, the regularization term can be determined as the intensity difference between neighboring voxels, which is given by $$U(p) = \sum_j \sum_{k \in \aleph_j} w_{jk} \psi_\delta(p_j - p_k),$$

wherein $\psi_\delta(t)$ is the penalty function, $\delta$ is a parameter that controls the smoothness of the penalty function, $w_{jk}$ is the weighting factor related to the distance between voxel j and voxel k in the neighborhood $\aleph_j$. An example of $\psi_\delta(t)$ is the Huber function, which can be expressed as $$\psi_\delta(t) = \begin{cases} \frac{1}{2}t^2, & \delta \geq |t| \\ \delta|t| - \frac{\delta^2}{2}, & \text{otherwise} \end{cases}.$$

In addition to the Huber function, the regularization term U(p) can be a quadratic regularization term, a total variation minimization term, or any other regularization term.

In certain implementations, the above optimization problem can be solved by the separable paraboloidal surrogate (SPS) approach with acceleration by ordered subsets (OS), for example. In general any optimization method can be used to find the image that minimizes the cost function, including, for example, a gradient-descent method or other known methods. Further examples of optimization methods that can be used to minimize the cost function can include an augmented-Lagrangian method, an alternating direction-method-of-multiplier method, a Nesterov method, a preconditioned-gradient-descent method, an ordered subset method, or a combination of the foregoing.

The above examples of denoising and smoothing methods have been provided as non-limiting examples. Variations of the above implementations for generating the stack of images having different noise and smoothing characteristics can be used without departing from the spirit or essential characteristics thereof, as will be understood by those skilled in the art.

Methods of generating a stack on images with different amounts or degrees of smoothing/denoising are discussed above. Now, we turn to the methods of combining the various images of the stack to generate a blended image.

As discussed above, tradeoffs exist between reducing noise and maintaining resolution. The outcome of a clinical procedure or diagnosis can depend on the image quality and how well adapted a reconstructed image is to the given application. That is, the optimal tradeoff between noise and resolution can be different depending on the clinical applications and organ being imaged. For example, more denoising/smoothing (i.e., a larger contribution from images having large smoothing parameters β) is preferred for suppressing noise in soft-tissue images, whereas less denoising/smoothing (i.e., a larger contribution from images having small smoothing parameters β) is preferred for preserving resolution in order to resolve finer features in lung images, for example.

Determining an optimal smoothing parameter β can be challenging because the optimal value for the smoothing parameter β can depend on the content to be viewed. That is, a single value for the smoothing parameter β might not be optimal for all clinical or detection tasks, or even for one detection tasks but for all of the regions within a single image. For example, when different types of regions (e.g., lung regions and soft-tissue regions) are displayed within a single image, it can be beneficial to segment the image into regions, and apply regions-adaptive blending to generate a blended image in which the relative weighting between images with small and large smoothing parameters β varies by region. This regions-adaptive blending can achieve the best resolution to the noise tradeoff on a region-by-region basis.

Returning to FIGS. 1A, 1B, 2A, and 2B, FIGS. 1A and 1B (2A and 2B) show the same lung (soft-tissue) region for two CT images generated using different values for the regularization parameter β. In these four figures, the images are from a slice of a reconstructed chest image generated using an IR method based to minimize a cost function that includes a regularization parameter β. The CT image used to generate the slices shown in FIGS. 1A and 2A was reconstructed using a small smoothing parameter β (i.e., the regularization parameter β method was small), whereas the CT image used to generate the slices shown in FIGS. 1B and 2B was reconstructed using a large smoothing parameter β.

FIGS. 1A and 1B show the lung region displayed using a window width (WW) of 1500 Hounsfield Units (HU) and a window level (WL) of −400 HU, which are standard width and level settings used to view lung regions. As observed in FIG. 1A, the resolution obtained using the small smoothing parameter is adequate for observing the fine features in the lungs, but the poorer resolution exhibited in FIG. 1B, which is due to using the large smoothing parameter, makes the fine features more difficult to observe than in FIG. 1A. Further, the wider window width of 1500 HU signals that a larger noise level can be tolerated without masking or obscuring the signal. Thus, generating the CT image using a small regularization parameter β is optimal for lung regions.

On the other hand, FIGS. 2A and 2B show the soft-tissue region displayed using a WW of 400 HU and a WL of 40 HU, which are standard width and level setting used to view soft-tissue regions. As observed in FIG. 2B, the noise present then using the small smoothing parameter tends to obscure the features of the tissue, increasing the difficulty of clinical diagnosis. Also, the narrower window width of 400 HU of the display settings signals that a less noise can be tolerated before significantly masking or otherwise obscuring the signal. Thus, generating the CT image using a large regularization parameter β is optimal for soft-tissue regions.

Given the above-identified tradeoff space between resolution and noise and given that optimality within the tradeoff space can depend on which type of tissue/organ is being imaged and depend on the application for which the CT image is being used, the methods herein dynamically adapt the displayed image according to signals (from the user and from the CT image itself) regarding the content/context being displayed. This is achieved by first acquiring a stack of images, each image having a different degree of smoothing/denoising. Then blending images from the image stack according to respective weights, which depend on the displayed content. That is, a blended image is generated and displayed using weighted combination of the images from the image stack, and the weighting depends on indicia of the image content.

In certain implementations, the weights for the weighted combination images are determined according to the display parameters (e.g., the window width and/or slice thickness) selected by a user. For example, on one hand, when a user chooses to display a slice of a reconstructed image using display settings for soft tissue with a WW of 400 HU and a WL, of 40 HU, then the weights for the blended image can be selected to have greater contributions from those of the stack images with large smoothing parameters. On the other hand, when a user chooses to display a slice of a reconstructed image using lung settings, the weights for the blended image can be selected to have greater contributions from those of the stack images with small smoothing parameters.

In certain implementations, the weights can vary as a function of position within the blended image (i.e., spatially-varying weights or region-adaptive weights), and these spatially-varying weights can be used to increase the contributions of large-smoothing-parameter images to the blended image in regions identified as having characteristics of soft tissue and bone, while increasing the contributions of small-smoothing-parameter images in regions identified as having characteristics of lung, for example.

The methods described herein are advantageous because a single smoothing parameters in not necessarily optimal for all detection/imaging tasks or for all regions. When the same data is used for multiple applications with corresponding image display parameters (e.g., the WW and WL), reconstructing a new image or applying a new post-reconstruction denoising method each time the display parameters are changed is impractical. However, the same effect (i.e., optimizing the noise and resolution based on the display parameters) can be achieved by changing the weights/blending between two or more images from the image stack, which is not impractical.

For example, returning to the non-limiting example of blending two CT images from an image stack (i.e., the small-smoothing-parameter image $p^{(\beta S)}$ and the large-smoothing-parameter image $p^{(\beta L)}$ to generate the blended image $p^{(Blended)}$, the two stack images $p^{(\beta S)}$ and $p^{(\beta L)}$ occupy different points within the resolution-noise tradeoff spaces (i.e., point "A" in the tradeoff space corresponding to $p^{(\beta S)}$ and point "B" corresponding to $p^{(\beta L)}$. Therefore, it is possible to generate a blended image $p^{(Blended)}$ at any point along a line segment in the tradeoff space extending from point "A" to point "B." Translations along this line segment are achieved by merely changing the relative weights applied to the two images of the stack. That is, the relative weights used to generate the blended image determine where the blended image is positioned within the tradeoff space along the line segment between points "A" and "B." Thus, the blending weights (i.e., the weights applied to the images of the stack) can be adjusted according to what is optimal for different regions and display parameters.

Further, a third CT image in the stack corresponding to a point "C" on the tradeoff space that is not on the line same line as points "A" and "B" would allow a blended image to occupy any point within a triangle defined by points "A," "B," and "C." Additionally, the stack of images can include more than three images, with the corresponding generalizations of the features described herein (e.g., the possible combinations for a stack of four images the blended image occupies a quadrilateral in the tradeoff space) without departing from the spirit or essential characteristics thereof, as will be understood by those skilled in the art.

This blending of the stack images can be seamless integrated into the clinical workflow. For example, streamlining this process so that it occurs automatically when display parameters are changed make it conducive for a clinical workflow, in which a doctor needs to focus on tasks other than changing the smoothing/denoising parameters. Accordingly, to avoid needless complicating a user interface, in certain implementations, the adjustment of the blending parameters can be tied directly to the display parameters or otherwise automated based on available signals and information. Thus, the user interface does not become needless complicated and the optimization of the displayed CT images can be optimized without frequent and/or complicated user interactions, which would reduce productivity by distracting clinicians from their primary tasks.

Figure 3:
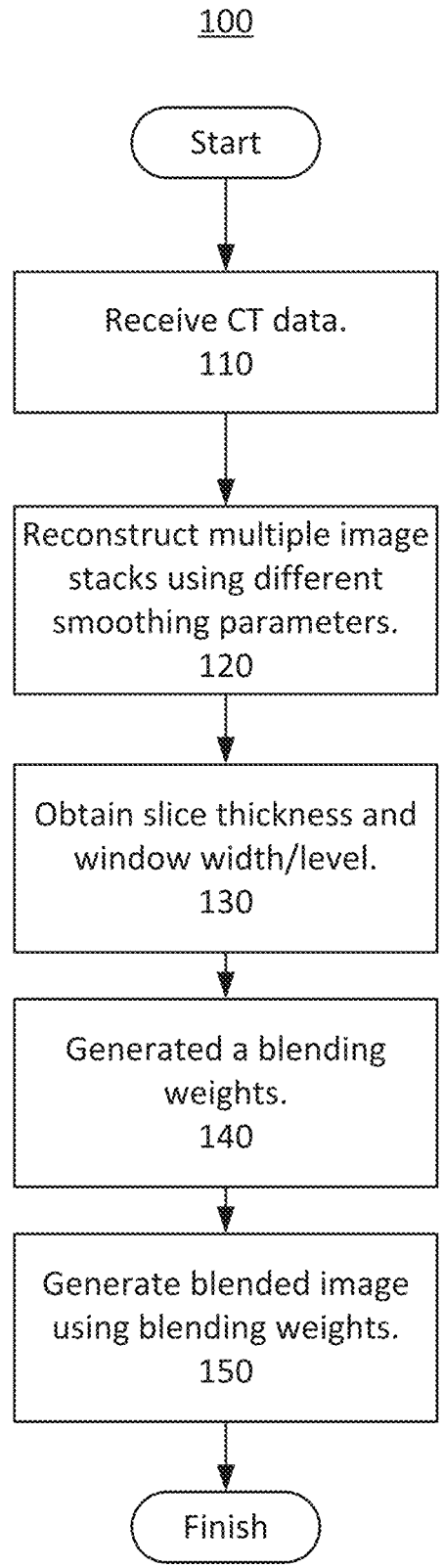
FIG. 3 shows a flow diagram of a method of generating a blended image based on the content/context of a CT image, according to one implementation.

FIG. 3 shows a flow diagram of a method 100 for generating a blended image from a stack of images corresponding to different smoothing parameters (the term "smoothing parameter" is used as a short hand for "smoothing/denoising parameter" and is interchangeable therewith).

Accordingly, the methods described herein provide context-oriented blending of a stack of images, each representing a different point within a tradeoff space between noise and resolution. In the stack, multiple images are generated to have different degrees of smoothing/denoising, and the images can be respectively identified using different values of a smoothing/denoising parameter (e.g., by reconstructing the CT images using a same IR method and cost function but with different values for the regularization parameter $\beta$).

In step 110 of method 100, projection data from a CT scan is obtained.

In step 120 of method 100, CT images are acquired representing reconstructions from the projection data. These CT images form a stack of images each having a respective smoothing parameter that is different from the other images in the stack. Any of the reconstruction methods as well as any of the per- and post-reconstruction denoising methods discussed below can be used to generate the CT images in the stack, and any other known methods of generating denoised CT images can also be used to generate the images in the stack.

In certain implementations, the smoothing/denoising parameter can be a vector including multiple values representing different characteristic of the respective images of the stack (e.g., a first value can represent a noise level and a second value can be a figure of merit to represent the resolution). Then, the weighting value $\alpha$, which is discussed below, can be a function with multiple inputs to weight the stack of images according to the content/context of the image and the multiple values of the smoothing/denoising parameter, which is a vector.

In step 130 of method 100, signals indicating the content/context of the displayed image (i.e., content/context indicia) are obtained. In certain implementations, the content/context indicia can be one or more display settings, such as the slice thickness, the window width, and the window level. In certain implementations, the content/context indicia can be a map of the regional average of the attenuation density. Further, in certain implementations, these content/context indicia can be a segmentation of the image into tissue types. Moreover, in certain implementations, the content/context indicia can be information indicating a use/application/procedure intended for the CT scan or displayed image, or the content/context indicia can be information regarding which body part of the patient is being imaged. Additional variations or combinations of the content/context indicia can be used without departing from the spirit or essential characteristics thereof, as will be understood by those skilled in the art.

Figure 4A:
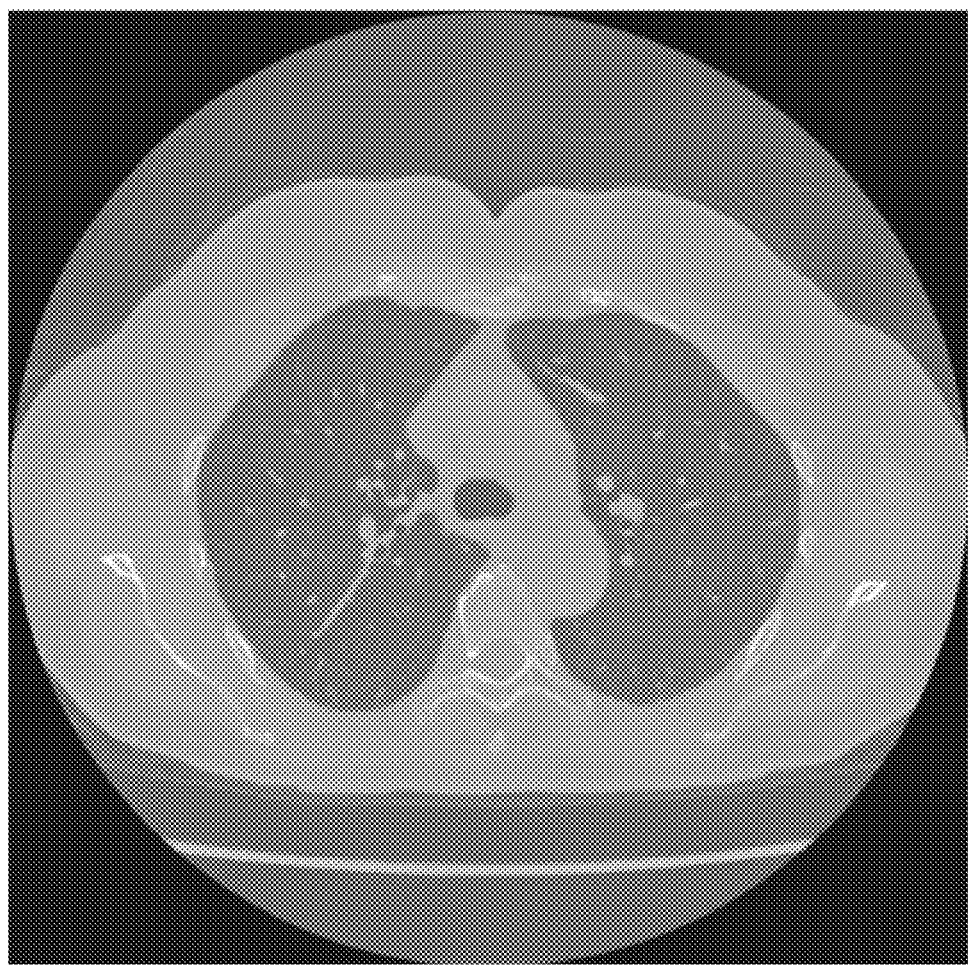
FIG. 4A shows a two-dimensional (2D) image of a CT slice displayed using default settings (i.e., WL=−297.5 HU and WW=3497 HU), according to one implementation.
Figure 4B:
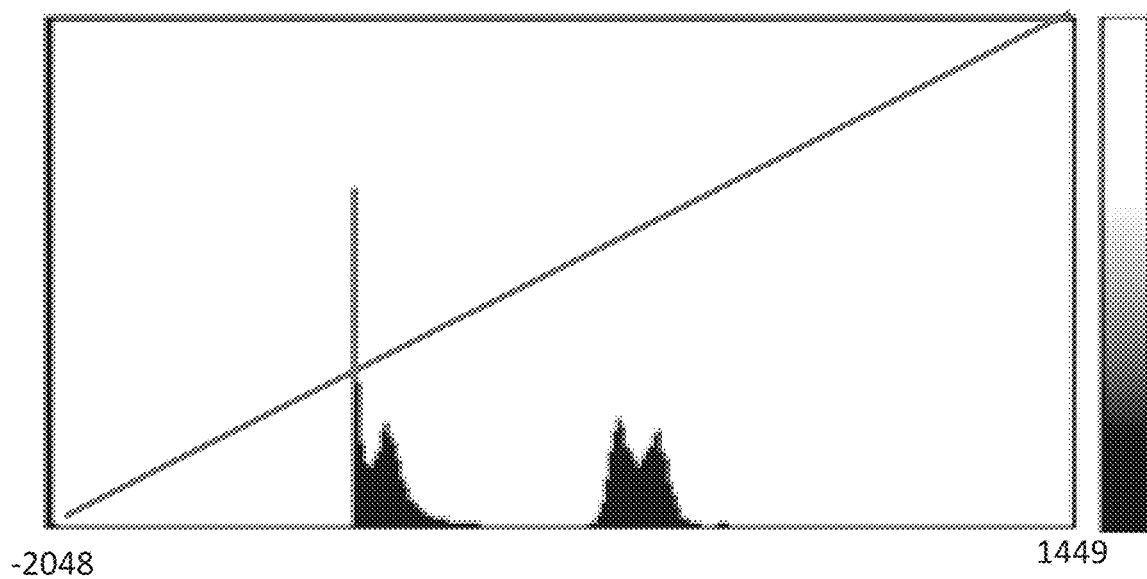
FIG. 4B shows a histogram of the CT slice binned according to HU values, in which HU values are represented along the horizontal axis with counts of voxels in the respective HU bins represented along the left vertical axis; on the right vertical axis is a color legend and, in the default display settings, the HU values are related to the colors in the color legend by the line superimposed over the histogram.
Figure 5A:
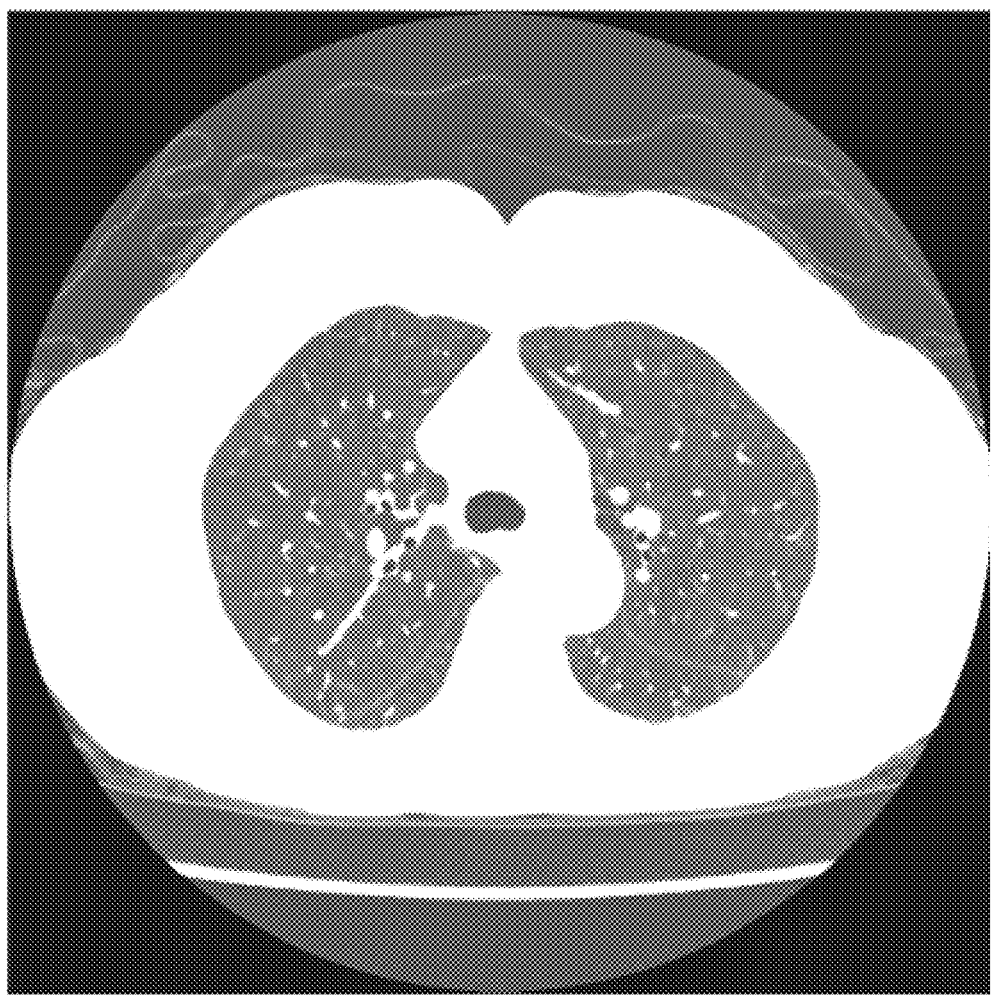
FIG. 5A shows a 2D image of the CT slice displayed using the lung settings.
Figure 5B:
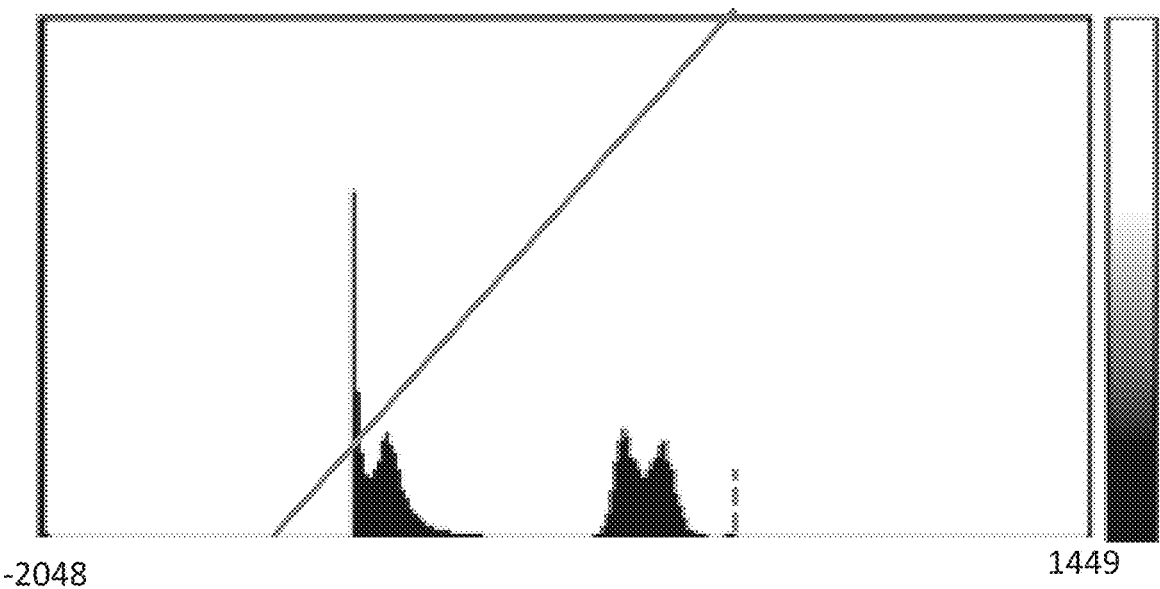
FIG. 5B shows the histogram of the CT slice together with the line that translates HU values to colors according to the lung settings.
Figure 6A:
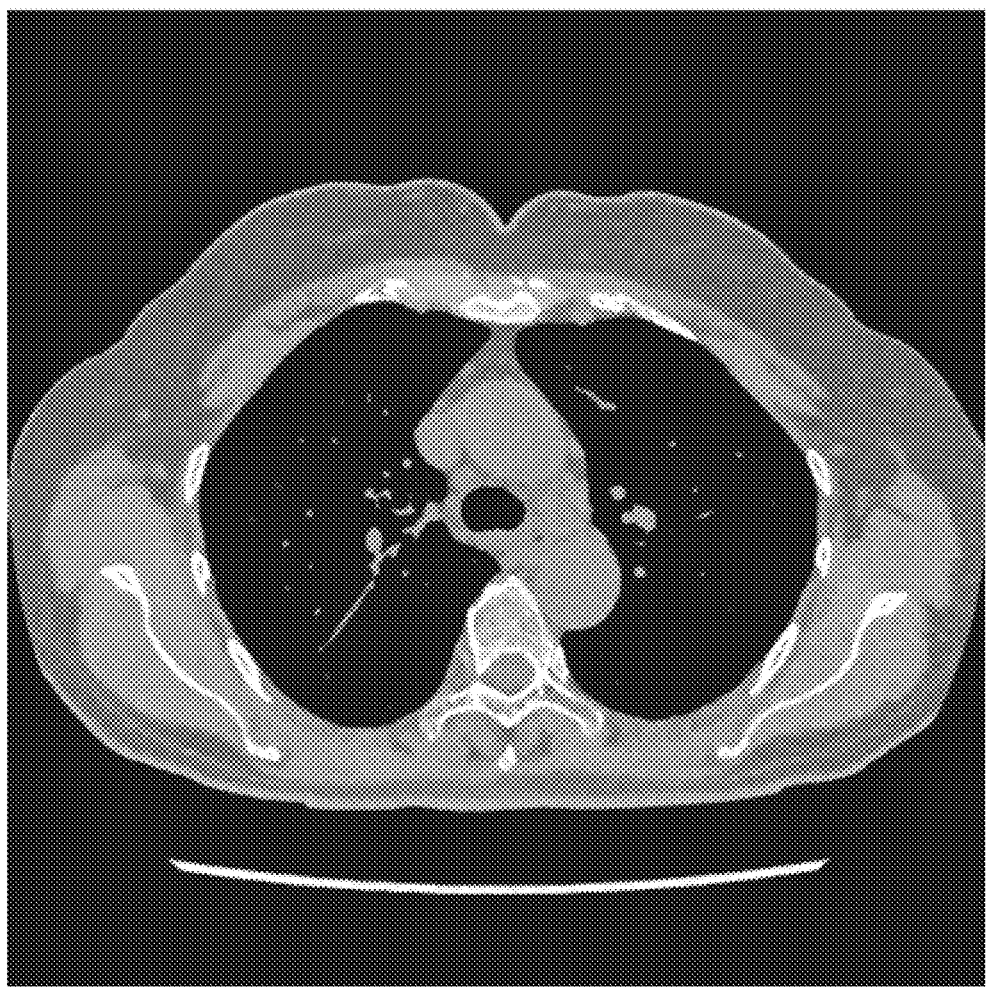
FIG. 6A shows a 2D image of the CT slice displayed using the soft-tissue settings.
Figure 6B:
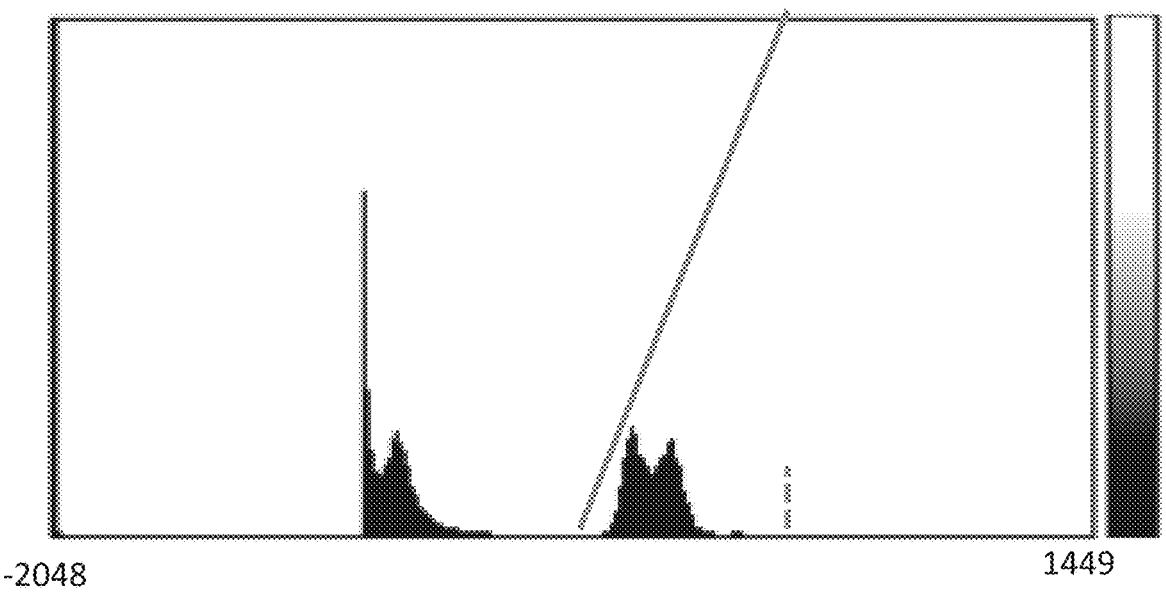
FIG. 6B shows the histogram of the CT slice together with the line that translates HU values to colors according to the soft-tissue settings.

Consider, for example, the use of the window width and slice thickness as content/context indicia. FIGS. 4A, 4B, 5A, 5B, 6A, and 6B illustrate the effect of choosing among various window settings. FIGS. 4A, 5A, and 6A respectively show two-dimensional views for a same slice of a chest CT image, but using different WW and WL settings in each image: (i) FIG. 4A uses default settings (i.e., WW=−297.5 HU and WL=3497 HU); (ii) FIG. 5A uses lung settings (i.e., WW=−400 HU and WL=1500 HU); and (iii) FIG. 6A uses soft-tissue settings (i.e., WW=400 HU and WL=40 HU). FIGS. 4B, 5B, and 6B respectively show a histogram of voxel counts for the slice binned according HU value. Additionally, on the right hand side, each of these figures includes a color legend of the of the HU values in the corresponding slice image and includes a line relating the HU values to the colors represented in the color legend. As discussed above and as illustrated by FIGS. 4A, 4B, 5A, 5B, 6A, and 6B, the optimal tradeoff between resolution and noise can depend on the display settings.

The window width and slice thickness inform optimal tradeoff between noise and resolution for several reasons. First, as discussed above, larger slice thicknesses correspond to reductions in noise due to the averaging of multiple voxel layers (e.g., shot noise in a Poison distribution is reduced as the square root of the number of voxel layers). Second, a larger window width is representative of larger signal and a greater tolerance for noise. Thus, the window width and slice thickness inform the optimal tradeoff between noise and resolution under the logic that noise becomes less significant as the window width becomes larger and/or the noise is reduced due to voxel-layer averaging, shifting the optimal tradeoff away from noise suppression and towards better resolution. On the other hand, in the absence noise reduction due to voxel-layer averaging, as the window width becomes narrower noise becomes more significant, and, therefore, the optimal tradeoff shifts towards increased noise suppression and away from better resolution.

In addition to window width and slice thickness, other factors and considerations can also inform the logic determining the optimal tradeoff. For example, when various content/context indicia indicate that the displayed image is being used for brain trauma diagnosis, strong smoothing is desired in a soft tissue region to reveal internal bleeding while reduced smoothing is desired in bone regions to reveal fractures.

In a different application for lung imaging, super-resolution reconstruction is desired to maintain details in lung regions while a pseudo normal-resolution image can be generated from the super-resolution reconstruction for diagnosing soft-tissue regions.

When the content/context indicia indicate that the displayed image is being used for a CT angiography application, high resolution is desired for vessels and low noise is desired in other regions.

Similarly, when the content/context indicia indicate that the displayed image is being used for a contrast enhanced CT application, high resolution is desired in the contrast-enhanced region while low noise is desired in other regions.

In each of these applications, the optimal tradeoff can be variously and automatically inferred from one or more of the content/context indicia discussed above or variation thereof as would be understood by a person of ordinary skill in the art. For example, Table 1 shows a correspondence between a few content/context indicia corresponding to the display settings and various applications for CT imaging.

TABLE 1

Various applications for CT imaging and their corresponding display settings.

| Application | Window Level (WL) | Window Width (WW) |
|---|---|---|
| Brain - Soft tissue | 40 | 80 |
| Chest | 40 | 400 |
| Abdomen | 60 | 400 |
| Lung | −400 | 1500 |
| Brain - Bone | 480 | 2000 |

In step 140 of method 100, the blending weights) a is generated based on the content/context indicia.

In certain implementations, each of the smoothing/denoising parameters corresponding to an image in the stack can be optimized for a particular detection task (e.g., the detection of long nodules or the detection of lesions in soft tissue).

Then, depending on user defined inputs related to the desired diagnosis (e.g., the WW and slice thickness), a blending weight α (or more generally as described below a blending map) is generated using weights corresponding to the user inputs. In certain implementations, the blended image is generated automatically based on the WW and the slice thickness. Additionally, in certain implementations, blending is performed using a spatially varying blending map; the blending weight of each voxel is determined by a blending map that is obtained from classifying different organs in a reconstructed CT image (e.g., one or more of the images in the image stack).

In certain implementations, the blended image is generated using a single value for blending weight α (e.g., the weight of the first image of the stack is α and the weight of the second image of the stack is (1-α)), and the blending weight α is a function of only two input variables: the first variable being the window width variable ww and the second variable being the slice thickness variable st.

For example, when the blended image $p^{(Blended)}$ is a weighted summation of a small-smoothing-parameter image $p^{(\beta S)}$ and a large-smoothing-parameter image $p^{(\beta L)}$, then blending weight α can be given by the equation $$\alpha = \begin{cases} 0, & (ww < \mu_{min}) \cap (st = 1) \\ \frac{ww - \mu_{max}}{\mu_{min} - \mu_{max}}, & (\mu_{min} \le ww \le \mu_{max}) \cap (st = 1), \\ 1, & (ww > \mu_{max}) \cup (st > 1) \end{cases}$$

wherein $\mu_{min}$ is a minimum value of the window width (e.g., 420 HU) and $\mu_{max}$ is a maximum value of the window width (e.g., 1200 HU). In this implementation, the two images $p^{(\beta S)}$ and $p^{(\beta L)}$ are blended with blending weight α determined by the window width ww and slice thickness st currently selected by the user for the displayed image. In the equation above, the window width variable ww is in terms of HU and the slice thickness variable st is in terms of a number of voxel layers. When α=1, the blended image $p^{(Blended)}$ is entirely the small-smoothing-parameter image $p^{(\beta S)}$, whereas the blended image $p^{(Blended)}$ is entirely the large-smoothing-parameter image $p^{(\beta L)}$ when α=0. The above equation expresses, in part, the logic that noise becomes less significant and is not a primary concern when either (i) the window width is large or (ii) a larger slice thickness causes the noise to be reduced due to averaging multiple layers of voxels. Therefore, when at least one of these conditions is met, the optimal noise-resolution tradeoff is skewed in favor of improved resolution by increasing contributions of the small-smoothing-parameter image $p^{(\beta S)}$ in the blended image.

On the other hand, a narrower window width indicates that the signal is likely to have a small amplitude (e.g., the features of interest have low contrast—small changes in HU values), increasing the importance of noise suppression by using a larger smoothing parameter. And this is especially true in the absence noise suppression due to layer averaging (i.e., when the slice thickness is small, corresponding to a single layer of voxels). Therefore, in this case, the optimal tradeoff shifts towards a blended image having increased contributions from the large-smoothing-parameter image $p^{(\beta L)}$.

Variations of this implementation can be used without departing from the spirit or essential characteristics thereof, as will be understood by those skilled in the art.

Figure 7:
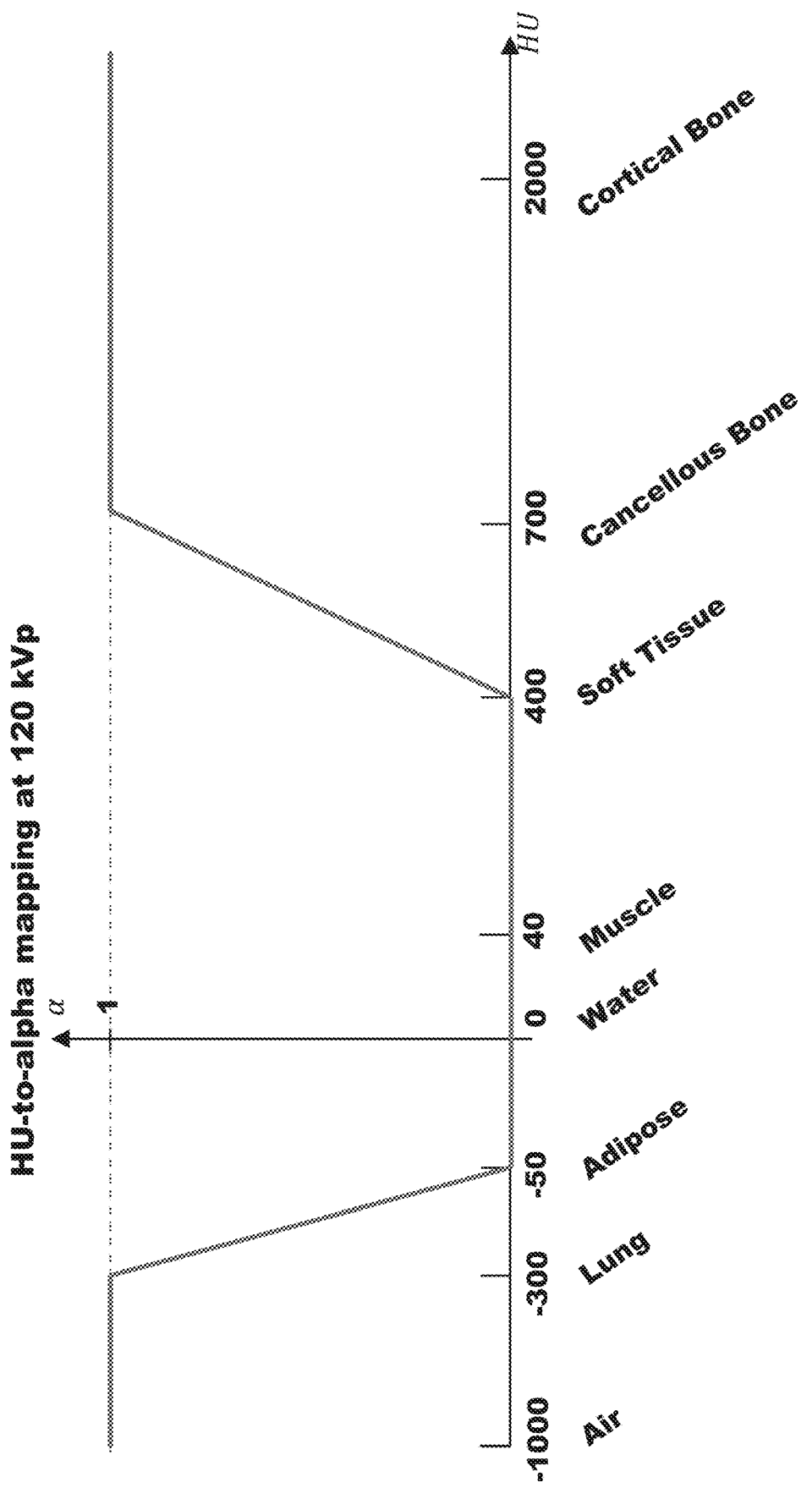
FIG. 7 shows a plot of an example of a weighting function representing a weighting value α along the vertical axis and an attenuation density in HU along the horizontal axis, the weighting value α being a weight used for combining a stack of two images generated using different smoothing/denoising parameters, according to one implementation.
Figure 8:
FIG. 8 shows a 2D map of the weighting value α as a function of position within the 2D image of the CT slice, according to one implementation.

In certain implementations, the blending weight α can be a blending map representing blending ratio that has a spatial dependence, as shown in FIG. 8. FIGS. 7 and 8 both relate to blending maps. FIG. 7 illustrates an example of a function for blending weight α, along the vertical axis, as a function of an average HU value within a given region. The average HU value can be determined using any one or a combination of images from the stack.

Consider for example the case of a stack containing only two images, the processes described below for determining the average HU values can be applied to the large-smoothing-parameter image $p^{(\beta L)}$ because the large-smoothing-parameter image $p^{(\beta L)}$ already exhibit a significant amount of smoothing, which is an averaging over nearby voxels. Therefore, calculating the average HU values from the large-smoothing-parameter image $p^{(\beta L)}$ reduces the amount of additional smoothing required to obtain the average HU values.

For example, the average HU value can be calculated using a window function (e.g., a Gaussian, Hann, Hamming, Blackman-Harris, or other window function known in signal processing) to weight the averaging of surrounding pixels/voxels to calculate the local average HU value for each with the reconstructed images of the stack. This can be performed as a convolution for example (i.e., low-pass filtering).

Alternatively, the image space can be segmented using, e.g., a threshold and region growing method or any other known segmentation method, and each segmented region can be averaged to obtain an average HU value for each of the segmented regions. In certain implementations, transitions between regions can be smoothed, e.g., using a feathering function, a spline function, an arctangent function, or any other method known to smooth transitions between regions.

Further variations of determining the averages HU value can be used without departing from the spirit or essential characteristics thereof, as will be understood by those skilled in the art.

Returning to FIG. 7 and having determined the average HU values for the respective voxels of the blended image, blending weights α for the respective voxels are generated using a lookup table or are calculated using a function such as the function shown in FIG. 7. The blending weight α in FIG. 7 assumes a stack having only two images, such that when α=1 the blended image $p^{(Blended)}$ is entirely the small-smoothing-parameter image $p^{(\beta S)}$, and the blended image $p^{(Blended)}$ is entirely the large-smoothing-parameter image $p^{(\beta L)}$ when α=0. FIGS. 4A, 4B, 5A, 5B, 6A, and 6B illustrate that HU values of certain regions tend to cluster according to a region type, and this general association between HU values and region types is indicated by the labels along the horizontal axis of FIG. 7.

Additionally, in certain implementations, dual-energy CT or spectrally-resolved CT can be used to perform material decomposition, and the complementary information provided by material decomposition can be used together with or in place of average HU value for enhanced discrimination of region types and for the subsequent selection of the optimal position-dependent weighted combination of images from the stack to generate the blended image.

Further, variations of the blending weight α function including variations of the inputs (e.g, average HU value, material-component ratio, etc.) and the outputs (e.g., for N images in the stack there can be N−1 values of α per voxel to define the ratios between the N images) can be used without departing from the spirit or essential characteristics thereof, as will be understood by those skilled in the art.

FIG. 7 exemplifies the logic that different average HU values can be indicia of content/context, and, therefore, the average HU values can be used to determine the weightings used in generating the blended image. That is, which weighting is likely optimal can depend on the content in the region, which is indicated by the average HU value. As discussed above for Table 1, specific imaging regions and applications can have unique optimality conditions, and different clinical and procedural applications of CT imaging can use variations of the function shown in FIG. 7 relating average HU to the blending weight α.

For example, in brain trauma diagnosis, strong smoothing is desired in soft tissue region to reveal internal bleeding, while high resolution is desired in a bone region to reveal fractures. The function shown in FIG. 7 has advantages when used for the above-identified application, including exhibiting high resolution in bone region together with noise suppression in the soft-tissue regions. Further, the function shown in FIG. 7 advantageously exhibits high resolution in the lung regions.

In another example, in contrast enhanced CT, high resolution is desired in contrast enhanced region while low noise is desired in other regions.

In certain implementations, the function relating average HU to blending weight α can depend on other content/context indicia of the clinical/procedural application or body part being imaged).

Variations in the shape of blending-weight function can be used without departing from the spirit or essential characteristics thereof, as will be understood by those skilled in the art.

FIG. 8 shows a slice of a blending map generated by applying the blending-weight function of FIG. 7 to the stack of CT image used in generating FIGS. 1A, 1B, 2A, and 2B. The blending-weight function can be expressed as $$\alpha_j = \begin{cases} 1, & -1000 < HU_j < -300 \\ \dfrac{HU_j - (-50)}{-300 - (-50)}, & -300 \le HU_j \le -50 \\ 0, & -50 < HU_j < 400 \\ \dfrac{HU_j - 400}{700 - 400}, & 400 \le HU_j \le 700 \\ 1, & 700 < HU_j \end{cases},$$

wherein $HU_j$ is the average HU value at the voxel indicated by index j, and $\alpha_j$ is the blending weight α corresponding to index j. According to this function, FIG. 8 shows that a small amount of smoothing together with high resolution is selected in the lung regions, but most of the soft-tissue regions is optimized to suppress noise by using a large amount of smoothing/denoising. The front of the chest region is in the transition range between −300 HU to −50 HU and represents a compromise between high resolution and high noise reduction.

In step 150 of method 100, the blended image is generated by the weighted combination of images from the stack. For example, the blended image can be generated by performing a weighted sum of the images from the stack.

For example, when the stack has two images and the blending weight α(ww, st) is a function of the window width variable ww and the slice thickness variable st, the blended image can be generated using the expression $$p^{(Blended)} = p^{(\beta S)}[\alpha(ww, st)] + p^{(\beta L)}[1 - \alpha(ww, st)].$$

Additionally, when a blending map $\alpha_j(HU_j)$ is used (e.g., with the HU-to-alpha mapping shown in FIGS. 7 and 8), then the blended image can be given by the equation $$p_j^{(Blended)} = \alpha_j p_j^{(\beta S)} + (1 - \alpha_j) p_j^{(\beta L)},$$

wherein $p_j^{(Blended)}$, $p_j^{(\beta S)}$, and $p_j^{(\beta L)}$ are respectively the $j^{th}$ voxels of the blended image, small-smoothing-parameter image, and the large-smoothing-parameter image.

When a blending map is used, the blended image is a combination of images from the stack, wherein the relative contributions among the images from the stack can vary voxel by voxel. Thus, spatially varying smoothness/denoising can be achieved to obtain an optimal resolution to noise tradeoff in every region of the blended image. Since the blending ratio is determined automatically, it does not require the user to adjust smoothing strength or blending ratio while navigating through different regions, and thus provides a simple and seamless user experience.

Variations of step 150 including, three or more images in the stack and different weighted combinations of the images in the stack (e.g., weighted arithmetic averaging, weighted geometric averaging, weightings incorporating that a functions of a figure of merit for the noise and/or resolution, etc.) can be used without departing from the spirit or essential characteristics thereof, as will be understood by those skilled in the art.

FIG. 9 shows (center) a reconstructed image generated using the blending map illustrated in FIG. 8. Also shown in FIG. 9 is a magnification (upper left) of the soft-tissue region represented in FIGS. 2A and 2B displayed using the soft-tissue settings, and a magnification (lower right) of the lung region represented in FIGS. 1A and 1B displayed using the lung settings. Comparing FIG. 9 with FIGS. 1A, 1B, 2A, and 2B reveals that, using method 100 with a blending map implementation, the desirable aspects of FIG. 1A and the desirable aspects of FIG. 2B have been combined within a single blended image. That is, method 100 produces a single image with low noise in the soft tissue region while preserving high resolution in the lung regions.

Accordingly, by method 100, a blended image can be generated automatically from a stack of two or more reconstructed images having different degrees of smoothing/denoising. Further, the blended image can be generated and displayed without additional input or burden on a user, eliminating the need to adjust the smoothing parameter or blending weight manually. Further, the tradeoff between resolution and noise can be simultaneously optimized in all regions of interest.

Figure 10:
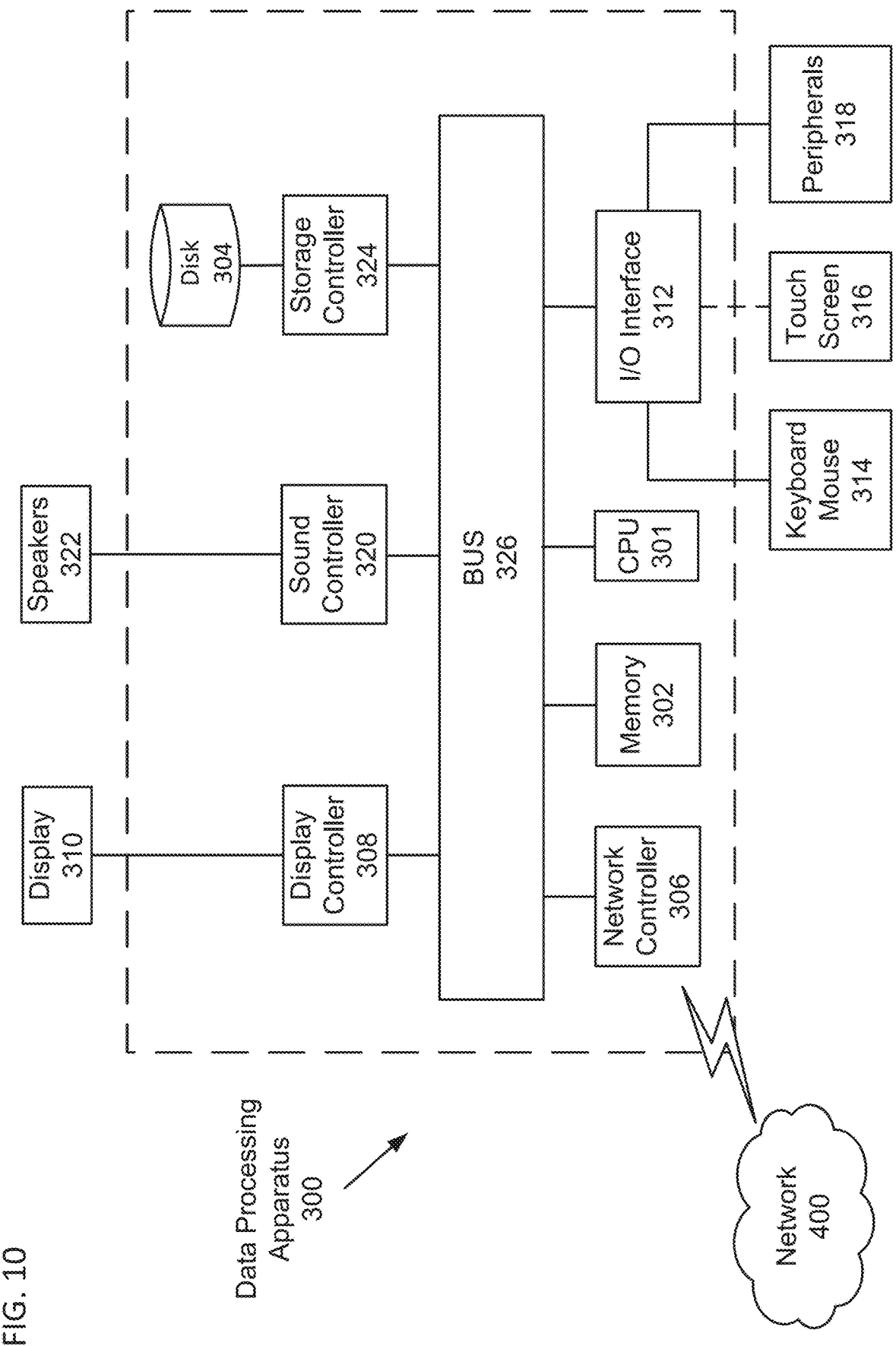
FIG. 10 shows a diagram of a data-processing apparatus for performing the methods described herein, according to one implementation.

Next, a hardware description, according to exemplary embodiments, is described with reference to FIG. 10 for a data-processing apparatus 300 for processing the CT projection data and the stack of reconstructed images by performing method 100 and the various processes herein. In FIG. 10, the data-processing apparatus 300 for processing CTP data includes a CPU 301 which performs the processes described above, including method 100 shown in FIG. 3, the processes described herein, and variations as would be known to a person of ordinary skill in the art. The process data and instructions may be stored in memory 302. These processes and instructions may also be stored on a storage medium disk 304 such as a hard drive (MD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the data-processing apparatus 300 communicates, such as a server or computer.

Further, the claimed advancements may be provided as a utility application, background daemon, or component of an operating system, or combination thereof, executing in conjunction with CPU 301 and an operating system such as Microsoft Windows 7, UNIX, Solaris, LINUX, Apple MAC-OS and other systems known to those skilled in the art.

CPU 301 may be a Xenon or Core processor from Intel of America or an Opteron processor from AMD of America, or may be other processor types that would be recognized by one of ordinary skill in the art. Alternatively, the CPU 301 may be implemented using a GPU processor such as a Tegra processor from Nvidia Corporation and an operating system, such as Multi-OS. Moreover, the CPU 301 may be implemented on an FPGA, ASIC, PLD or using discrete logic circuits, as one of ordinary skill in the art would recognize. Further, CPU 301 may be implemented as multiple processors cooperatively working in parallel to perform the instructions of the inventive processes described above.

The data-processing apparatus 300 in FIG. 10 also includes a network controller 306, such as an Intel Ethernet PRO network interface card from Intel Corporation of America, for interfacing with network 400. As can be appreciated, the network 400 can be a public network, such as the Internet, or a private network such as an LAN or WAN network, or any combination thereof and can also include PSTN or ISDN sub-networks. The network 400 can also be wired, such as an Ethernet network, or can be wireless such as a cellular network including EDGE, 3G and 4G wireless cellular systems. The wireless network can also be WiFi, Bluetooth, or any other wireless form of communication that is known.

The data-processing apparatus 300 further includes a display controller 308, such as a NVIDIA GeForce GTX or Quadro graphics adaptor from NVIDIA Corporation of America for interfacing with display 310, such as a Hewlett Packard HPL2445w LCD monitor. A general purpose I/O interface 312 interfaces with a keyboard and/or mouse 314 as well as a touch screen panel 316 on or separate from display 310. General purpose I/O interface also connects to a variety of peripherals 318 including printers and scanners, such as an OfficeJet or DeskJet from Hewlett Packard.

A sound controller 320 is also provided in the parallel scalar-multiplication apparatus, such as Sound Blaster X-Fi Titanium from Creative, to interface with speakers/microphone 322 thereby providing sounds and/or music.

The general purpose storage controller 324 connects the storage medium disk 304 with communication bus 326, which may be an ISA, EISA, VESA, PCI, or similar, for interconnecting all of the components of the Parallel scalar-multiplication apparatus. A description of the general features and functionality of the display 310, keyboard and/or mouse 314, as well as the display controller 308, storage controller 324, network controller 306, sound controller 320, and general purpose I/O interface 312 is omitted herein for brevity as these features are known.

Figure 11:
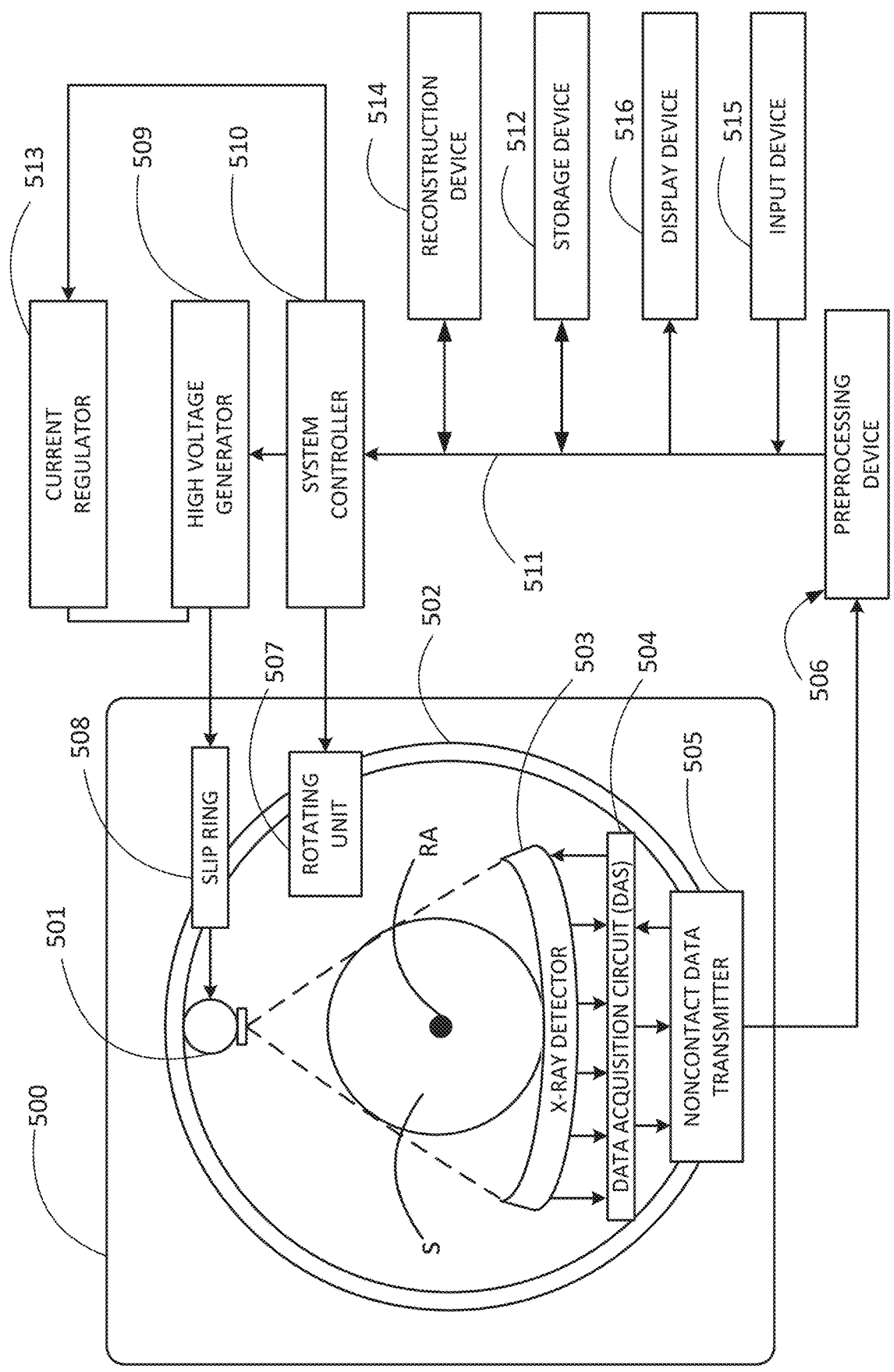
FIG. 11 shows a schematic of an implementation of a CT scanner.

FIG. 11 illustrates an implementation of the radiography gantry included in a CT apparatus or scanner. As shown in FIG. 11, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA. A rotating unit 507 rotates the annular frame 502 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A memory 512 stores the resultant data, which is also called projection data at a stage immediately before reconstruction processing. The memory 512 is connected to a system controller 510 through a data/control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing methods 100 and 200 for post-reconstruction processing and enhancement of reconstructed CT images.

The reconstruction device 514 can reconstruct CT images and can execute post processing of the reconstructed CT images, including methods 100 and 200 described herein. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example.

Post-reconstruction processing performed by the reconstruction device 514 can include filtering and smoothing the image, volume rendering processing, and image difference processing as needed. Further, the post-reconstruction processing can include jagged-edge removal and resolution enhancement using method 100 and/or 200. The image reconstruction process can be performed using known methods, including, e.g., filtered-backprojection, iterative reconstruction, algebraic reconstruction techniques, ordered subsets, and acceleration techniques. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL. Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
circuitry configured to
obtain a plurality of images representing respective computed tomography (CT) reconstructed images with different degrees of denoising,
receive one or more indicia indicating content and/or context of a display image to be displayed on a display,
determine weighting coefficients based on the one or more indicia,
combine the plurality of images using the weighting coefficients to generate a blended image, and
control a display to display the blended image as the display image.

2. The apparatus according to claim 1, wherein the circuitry is further configured to obtain the plurality of images having the respective denoising parameters by
reconstructing each of the plurality of images by optimizing respective cost functions, each cost function having a data fidelity term and a product between a regularization parameter and a regularization term, wherein
the regularization parameter is used to parametrize the different degrees of denoising of the respective images of the plurality of images.

3. The apparatus according to claim 1, wherein the circuitry is further configured to determine the weighting coefficients by
receiving an instruction to display the display image according to one or more display parameters, the one or more indicia including the one or more display parameters, and
determining the weighting coefficients based on the one or more display parameters.

4. The apparatus according to claim 1, wherein the circuitry is further configured to combine the plurality of images using the weighting coefficients by
summing, as a weighted summation, multiplication products of respective images of the plurality of images, respectively, with corresponding weighting coefficients of the weighting coefficients.

5. The apparatus according to claim 3, wherein the circuitry is further configured to determine the weighting coefficients based on the one or more indicia, wherein the on the one or more indicia include at least one of a window width of attenuation values to be displayed and a slice thickness of the display image.

6. The apparatus according to claim 5, wherein the circuitry is further configured to determine the weighting coefficients between a first image of the plurality of images and a second image of the plurality of images, for which the first image is denoised more than the second image, the weighting coefficients being determined such that, for relative contributions to the blended image of the first and second images, a contribution of the first image relative is increased relative to a contribution of the second image, when the window width becomes narrower, the contribution of the first image is increased relative to the contribution of the second image, when the slice thickness becomes thinner, the contribution of the second image is increased relative to the contribution of the first image, when the window width becomes wider, and the contribution of the second image is increased relative to the contribution of the first image, when the slice thickness becomes thicker.

7. The apparatus according to claim 1, wherein the circuitry is further configured to determine the weighting coefficients to be functions of a position, the position being a position within the blended image, and the weighting coefficients being determined by obtaining, using the one or more indicia, a spatially dependent parameter, which is a function of the position, mapping, for each of the positions within the blended image, a respective value of the spatially dependent parameter at a position to the weighting coefficients at the position based on one or more predefined functions to generate a weighting coefficients map, and combine the plurality of images using the weighting coefficients map by determining, for each of the positions in the blended image, a value of attenuation at a position in the blended image using the corresponding weighting coefficients of the weighting coefficients map at the position.

8. The apparatus according to claim 1, wherein the circuitry is further configured to determine the weighting coefficients so that:

when the one or more indicia indicate a brain trauma application, the weighting coefficients adjust a relative contribution to the blended image from images of the plurality of images to realize more smoothing and less noise in a soft-tissue region and to less smoothing and more noise in a bone region, when the one or more indicia indicate a lung imaging application, a first image of the plurality of images is generated to have a high-resolution and the weighting coefficients adjust the relative contribution to the blended image to be predominantly the first image in a lung region and in a soft-tissue region the relative contribution to the blended image realizes more smoothing and less resolution than in the lung region, when the one or more indicia indicate an angiography application, the weighting coefficients adjust the relative contribution to the blended image to realize less smoothing and more noise in a contrast-agent region and more smoothing and less noise elsewhere, and when the one or more indicia indicate a contrast-enhanced application, the weighting coefficients adjust the relative contribution to the blended image to realize less smoothing and more noise in a contrast-enhanced region and more smoothing and less noise elsewhere.

9. The apparatus according to claim 1, wherein the circuitry is further configured to determine the weighting coefficients, wherein the weighting coefficients are a blending map in which a value of the weighting coefficients depends on a position in the blended image, such that for each position in the blended image the weighting coefficients sum to a predefined constant, and values of the blending map are determined by one of averaging attenuation values in a neighborhood of one or more images of the plurality of images corresponding to a position in the blended image to generate an average attenuation, and applying a first function to the generated average attenuation to generate a value of the blending map corresponding to the position in the blended image, and segmenting one or more images of the plurality of images into regions according to a plurality of region types, and applying a predefined lookup table to assign values to the blending map according to a respective region type corresponding to the position in the blended image.

10. The apparatus according to claim 1, wherein the circuitry is further configured to determine the weighting coefficients, wherein the plurality of region types include two or more of a lung type, an air type, an adipose type, a water type, a muscle type, a soft-tissue type, a cancellous-bone type, a cortical-bone type, a brain-tissue type, and a bone type.

11. The apparatus according to claim 1, wherein the circuitry is further configured to determine the weighting coefficients using a first function relating an attenuation value to a value of the weighting coefficients, such that:

for large attenuation values, the first function outputs weighting coefficients that increase a relative contribution of a first image of the plurality of images that has less smoothing, for medium attenuation values, the first function outputs weighting coefficients that increase a relative contribution of a second image of the plurality of images that has more smoothing, for small attenuation values, the first function outputs weighting coefficients that increase the relative contribution of the first image, wherein the large attenuation values are greater than the medium attenuation values, which are greater than the small attenuation values, the first image has finer resolution and more noise than the second image, and a relative contribution represents a percentage of the blended image corresponding to an image of the plurality of images.

12. The apparatus according to claim 1, wherein the circuitry is further configured to obtain the plurality of images having the different degrees of denoising by one or more of generating the plurality of images using iterative reconstruction to minimize a cost function including a regularization term multiplied by a first constant, and the respective images of the plurality of images are generated using different values for the first constant, applying a post-reconstruction denoising method parameterized by a second constant to a reconstructed image, wherein the plurality of images are generated by noising the reconstructed image using different values for the second constant, and applying a pre-reconstruction denoising method parameterized by a third constant to a sinogram, wherein the plurality of images are reconstructed from a plurality of denoised sinograms, which are generated by denoising the sinogram using different values for the third constant.

13. The apparatus according to claim 1, wherein the circuitry is further configured to receive the one or more indicia, wherein the one or more indicia include one or more of a display setting of window width of a displayed attenuation, a display setting of window level of the displayed attenuation, a display setting of slice thickness, information of a clinical application, information of an imaged body part, and information of a patient.

14. The apparatus according to claim 9, wherein the circuitry is further configured to determine the weighting coefficients, so that the blending map is further based on information of a material decomposition.

15. A computed tomography (CT) scanner, comprising:
an X-ray source configured to emit X-rays;
a detector configured to receive the X-rays at a plurality of detector elements and generate projection data representing an intensity of the X-rays at the plurality of detector elements; and
circuitry configured to
  generate a plurality of images representing respective CT images reconstructed images from the projection data, each of the plurality of images having a different degree of denoising with respect to others of the plurality of images,
  receive one or more indicia indicating content and/or context of a display image to be displayed on a display,
  determine weighting coefficients based on the one or more indicia,
  combine the plurality of images using the weighting coefficients to generate a blended image, and
  control a display to display the blended image as the display image.

16. A method, comprising:
obtaining a plurality of images representing respective computed tomography (CT) reconstructed images with different degrees of denoising,
receiving one or more indicia indicating content and/or context of a display image to be displayed on a display,
determining weighting coefficients based on the one or more indicia,
combining the plurality of images using the weighting coefficients to generate a blended image, and
controlling a display to display the blended image as the display image.

17. The method according to claim 16, wherein the determining of the weighting coefficients further includes
representing the weighting coefficients as a blending map in which a value of the weighting coefficients depends on position in the blended image such that for each position in the blended image the weighting coefficients sum to a predefined constant, and values of the blending map are determined by one of
averaging attenuation values in a neighborhoods of one or more images of the plurality of images corresponding to a position in the blended image to generate an average attenuation, and applying a first function to the generated average attenuation to generate a value of the blending map corresponding to the position in the blended image, and segmenting one or more images of the plurality of images into regions according to a plurality of region types, and applying a predefined lookup table to assign values to the blending map according to a respective region type corresponding to the position in the blended image.

18. The method according to claim 16, further comprising
receiving an instruction to display the display image according to one or more display parameters, the one or more display parameters being included in the one or more indicia, and
  the determining of the weighting coefficients based on the one or more indicia further includes that the weighting coefficients are based on the one or more display parameters, wherein the one or more display parameters includes at least one of a window width of attenuation values of the display image and a slice thickness of the display image,
  the weighting coefficients change to increase a contribution to the blended image of a first image of the plurality of images relative to a contribution to the blended image of a second image of the plurality of images, when the slice thickness decreases or when the window width decreases, the first image being denoised more than the second image, and
  the weighting coefficients change to increase the contribution to the blended image of the second image relative to the contribution to the blended image of the second image when the slice thickness increases or when the window width increases.

19. The method according to claim 16, wherein
the determining of the weighting coefficients further includes that the weighting coefficients are functions of a position, the position being a position within the blended image, the weighting coefficients being determined by
  obtaining, using the one or more indicia, a spatially dependent parameter, which is a function of the position,
  mapping, for each of the positions within the blended image, a respective value of the spatially dependent parameter at a position to the weighting coefficients at the position based on one or more predefined functions to generate a weighting coefficients map, and
the combining of the plurality of images using the weighting coefficients is performed by determining, for each of the positions in the blended image, a value of attenuation at a position in the blended image using the corresponding weighting coefficients of the weighting coefficients map at the position.

20. A non-transitory computer readable storage medium including executable instruction, wherein the instructions, when executed by circuitry, cause the circuitry to perform the method according to claim 16.

* * * * *